United States Patent [19]

Pollack

[11] Patent Number: 4,853,377

[45] Date of Patent: * Aug. 1, 1989

[54] METHOD AND COMPOSITION FOR INCREASING PRODUCTION OF SEROTONIN

[76] Inventor: Robert L. Pollack, 8442 Chippewa Rd., Philadelphia, Pa. 19128

[*] Notice: The portion of the term of this patent subsequent to Mar. 17, 2004 has been disclaimed.

[21] Appl. No.: 165,444

[22] Filed: Feb. 29, 1988

Related U.S. Application Data

[63] Continuation of Ser. No. 25,002, Mar. 12, 1987, abandoned, which is a continuation-in-part of Ser. No. 787,502, Oct. 15, 1985, Pat. No. 4,650,789.

[51] Int. Cl.$^4$ .................... A61K 31/35; A61K 31/40; A61K 31/62; A61K 31/70

[52] U.S. Cl. ...................... 514/161; 514/23; 514/277; 514/356; 514/419

[58] Field of Search ............... 514/23, 161, 277, 356, 514/419

Primary Examiner—Stanley J. Friedman
Attorney, Agent, or Firm—Ratner & Prestia

[57] ABSTRACT

The production of the neurotransmitter serotonin is increased through administration of a therapeutic composition which includes L-tryptophan in combination with a salicylate, an ascorbate, calcium, magnesium, copper, pyridoxine, niacin and a carbohydrate such as fructose. Both the absolute free fraction and the relative amount of the albumin-bound fraction of serum L-tryptophan are increased so that transport of L-tryptophan from the blood plasma across the blood-brain barrier into the brain is increased. Once within the brain, L-tryptophan is converted to serotonin.

13 Claims, No Drawings

METHOD AND COMPOSITION FOR INCREASING PRODUCTION OF SEROTONIN

This application is a continuation of application Ser. No. 025,002, filed Mar. 12, 1987, now abandoned, which is a continuation-in-part application of application Ser. No. 787,502, filed Oct. 15, 1985, now U.S. Pat. No. 4,650,789.

Reference is made to the co-pending patent application of Robert L. Pollack and Lawrence Durst, application Ser. No. 007,121, filed Jan. 26, 1987 and to U.S. Pat. No. 4,639,465, of Robert L. Pollack and Lawrence Durst, issued Jan. 27, 1987.

BACKGROUND OF THE INVENTION

1. Field of the Invention

This invention relates generally to a dietary supplement for relieving physiological disorders and particularly relates to a composition which promotes the production of serotonin within the brain.

2. Description of Prior Developments

Attention has recently turned to nontraditional methods and compositions for treating various physiological disorders in an effort to provide relief in those instances where standard techniques have proven ineffective and where it is desired to avoid the undesirable side effects of conventional pharmaceutical compositions. One approach has been to attempt to provide relief through dietary supplementation of L-tryptophan (tryptophan).

Once within the brain, neurons convert tryptophan into the neurotransmitter serotonin. It has been found that an increase of tryptophan in the brain increases the brain's production of serotonin. Brain levels of serotonin have been shown to be linked to sleep, appetite, depression, and pain threshold. Disturbances in the brain causing reduced levels of serotonin have been linked to clinical (endogenous) depression, insomnia, excessive appetite, weight gain and lowered pain threshold.

While treatment of such disorders with supplemental tryptophan has heretofore produced positive results, there has been a wide range in the degree of relief achieved. Some patients appear to respond more favorably to such treatment than others for no previously known reason. Thus, complete relief has not consistently been assured by prior dietary tryptophan supplements. It is believed that these conventional supplements lack a complete combination of ingredients necessary to ensure the maximum relief achievable with every patient through tryptophan supplementation.

It is known that dietary supplementation of tryptophan increases the blood level of tryptophan and facilitates the passage of tryptophan across the blood-brain barrier into the brain. The increased amount of tryptophan in the brain permits a greater amount of tryptophan to be converted to serotonin.

In order for tryptophan to be converted to serotonin in the brain, it must cross a separating mechanism that exists between the blood vessels and the brain. To reach the brain, tryptophan requires a carrier transport mechanism in the form of a carrier protein which, literally, carries tryptophan across this very selective blood-brain barrier and into the brain. Not only is tryptophan carried by this transport mechanism, but other selected amino acids, called large neutral amino acids (LNAAs), are carried as well.

Tryptophan not only has to compete with the LNAAs for access to the transport carrier mechanism, it also has a lower affinity for the carrier system than does the LNAAs. To compound this situation further, tryptophan in foods is generally present in lower amounts than the LNAAs—particularly in animal proteins. All of these factors contribute to the amount of tryptophan that actually gets through to the brain, to be finally converted to serotonin.

There are numerous conditions, improper diet constitutes one of them, that can interfere with, and decrease, the amount of tryptophan that normally passes through the blood-brain barrier into the brain each day. This comes about when the ratio of tryptophan to LNAAs in the blood reaching the brain is lower than normal. This means that the number of molecules of tryptophan present at the blood-brain barrier is much smaller than the number of molecules of LNAAs present at the same blood-brain barrier. The LNAAs overwhelm the tryptophan such that very little tryptophan is provided passage into the brain as compared to the number of LNAAs that are provided passage.

In the attempt to correct this improper tryptophan/LNAA ratio, it was found that increasing the total protein intake obtained from normal dietary sources, in order to add more tryptophan to the system, results, paradoxically, in an even greater decrease in the amount of tryptophan reaching the brain. This is so because there are usually more LNAAs than there is tryptophan in food. Experimental studies have established the fact that increasing the amount of protein as food, in order to improve the tryptophan/LNAA ratio, only makes the tryptophan/LNAA ratio worse because of the greater intake of the LNAAs over the intake of the tryptophan.

With less tryptophan getting into the brain, less serotonin is formed, and a wide variety of disorders, including those noted above, begin to manifest themselves. Because these disorders stem from a biochemical imbalance involving the tryptophan-serotonin relationship, they cannot be corrected by any conventional medication. Such disorders are unmanageable by any conventional drug therapy because the drug does not address itself to the correction of this specific biochemical imbalance.

Accordingly, a need exists for a method and composition for transporting an effective dose of tryptophan across the blood-brain barrier into the brain and for promoting the conversion of tryptophan into serotonin. Moreover, a need exists for a composition which provides all the ingredients necessary to achieve the maximum relief possible through dietary supplementation of tryptophan.

SUMMARY OF THE INVENTION

The present invention has been designed as a dietary therapeutic composition including a combination of ingredients which will provide the proper and effective dietary supplementation of both free and albumin-bound tryptophan for increasing the production of serotonin in the brain. Increased serotonin production can decrease or eliminate chronic pain, particularly in those conditions where the pain stems from an unknown origin, and not due to any known medical, dental or psychological reason. Moreover, clinical depression, insomnia and appetite disorders may also be relieved or eliminated via such dietary supplementation.

The administration of pure tryptophan will help to improve the ratio of blood tryptophan to blood LNAAs, help to increase the amount of tryptophan that will enter the brain, and help to increase the serotonin level within the brain and raise the pain threshold level while concurrently relieving depression, insomnia and certain appetite-related disorders. The effectiveness of pure tryptophan in raising the pain threshold level and in relieving depression, insomnia and other disorders including excessive appetite can be improved with the addition of other specific dietary supplements as set forth below.

The oral administration of tryptophan in combination with several other operative ingredients taken under proper dietary conditions provides a supplementary intake of this particular amino acid which helps to correct an improper tryptophan/LNAA ratio. The dietary supplementation of the tryptophan-based composition described below, combined with an adjusted protein, low fat, higher carbohydrate intake, results in a significant reduction in any one or all unpleasant symptoms experienced by patients having low or insufficient brain levels of serotonin. When administered as an anorectic, the composition significantly reduces intake of all calorie laden nutrients including protein, fats and carbohydrates, thereby serving as an effective aid in any weight control program.

L-tryptophan is usually not transported in the blood in a free state, but rather in a bound or complexed form with the protein albumin, a plasma component. In fact, L-tryptophan is the only circulating amino acid that is significantly bound to human serum albumin. It has been shown that various salicylates displace tryptophan from its protein binding site with albumin in blood plasma thereby raising the free or unbound tryptophan concentration in the blood. The bond-breaking effect exerted by salicylates on the binding of tryptophan to albumin causes a greater availability of free tryptophan molecules for diffusion into body cells.

In humans, the ingestion of salicylates such as magnesium salicylate and aspirin causes a release of tryptophan from its binding site on serum albumin, and results in the presence of a free, unbound fraction of tryptophan within the blood. It has now been determined that it is primarily the free fraction of serum tryptophan which controls the concentration of brain tryptophan as well as the brain's production of serotonin. The greater the amount of the free or unbound tryptophan, the greater the amount of serotonin production.

The brain tryptophan level reflects brain serotonin turnover so that the resultant increase in the availability of circulating free tryptophan to the brain leads to an enhancement of brain serotonin synthesis.

A major aspect of the present invention is specifically directed to the addition of a salicylate, calcium, magnesium and ascorbic acid to a tryptophan-based composition so that both the level of serotonin within the brain is increased and the quality and strength of the nerve signals or impulses transmitted by this neurotransmitter is improved and strengthened.

In order to appreciate the specific selection and combination of ingredients described below, a brief description of the biochemical processes by which tryptophan is converted into serotonin is of value.

Generally, serotonin is produced within brain membranes by a process involving the interaction of the amino acid L-tryptophan with the enzyme tryptophan hydroxylase. More particularly, two separate enzymatic steps are necessary for the synthesis of serotonin (5-HT) from its natural precursor tryptophan. The first step involves the conversion of tryptophan into 5-hydroxytryptophan (5-HTP) via interaction with the enzyme tryptophan hydroxylase. The second step involves the decarboxylation of 5-HTP into 5-HT via aromatic amino acid decarboxylase.

It is the first step which is believed to present the greatest hurdle in the conversion of tryptophan to serotonin. Moreover, it is believed that this first step primarily affects the amount of serotonin produced within the brain. Accordingly, it is the first enzymatic step on which the present invention concentrates.

As stated, tryptophan must first be converted to 5-HTP by tryptophan hydroxylase. However, only a special activated form of tryptophan hydroxylase will bring about this conversion. This activated form is a phosphorylated form of tryptophan hydroxylase which is produced through the action of a calcium-dependent protein kinase. It is calcium which stimulates the kinase to posphorylate the tryptophan hydroxylase. Thus, the addition of calcium to the tryptophan composition ensures the adequate presence of calcium required to initiate the conversion of tryptophan to serotonin.

Another factor in the synthesis or conversion of tryptophan into serotonin involves the hydroxylation of tryptophan by the phosphorylated tryptophan hydroxylase. The rate-limiting step in the synthesis of serotonin is the hydroxylation step which is catalyzed by tryptophan hydroxylase. Once tryptophan crosses the blood-brain barrier into the brain, the tryptophan bonds with nerve membranes on serotoninergic neurons. At this point the tryptophan undergoes hydroxylation by accepting an OH group from the activated enzyme tryptophan hydroxylase, a copper-protein enzyme, which is present within the brain.

The hydroxylation of tryptophan is believed to involve the reduction of the calcium/kinase-activated tryptophan hydroxylase copper atoms and the reduction of a presently unknown enzyme group X also present on the enzyme. Thus, by providing supplemental ascorbic acid and copper according to the invention, the hydroxylation of tryptophan into 5-HTP is further facilitated. The reduction of the tryptophan hydroxylase takes place by the successive addition of single electrons to its copper atoms and to the enzyme group X from ascorbic acid. That is, tryptophan hydroxylase is a copper-protein complex that uses ascorbic acid as a reducing agent. Thus, by providing supplemental ascorbic acid and copper according to the invention, the hydroxylation of tryptophan into 5-HTP is further facilitated.

In short, calcium initially stimulates kinase to activate (phosphorylate) tryptophan hydroxylase. The tryptophan is then hydroxylated by the activated or phosphorylated tryptophan hydroxylase through reduction of copper via electron transfers from ascorbic acid.

To further ensure the efficacy of serotonin in relieving physiological disorders, magnesium is added to the composition, preferably along with calcium, to increase the bond strength between serotonin and the nerve membranes as well as to increase the total number of binding sites available to serotonin on the brain/nerve membranes. By increasing both the strength and the number of bonds between serotonin and the nerve membranes, a stronger nerve impulse or signal is transmitted by the passage of serotonin across the nerve synapses thereby resulting in a more pronounced physiological effect leading to more pronounced relief.

It is possible that the somewhat unpredictable results achieved by prior tryptophan-based compositions may be attributable to a lack of ascorbic acid, calcium and/or magnesium available in the patient's brain for the conversion of tryptophan to serotonin.

It is therefore an object of the invention to povide a method and composition for relieving physiological disorders through dietary supplementation of tryptophan in combination with other ingredients which facilitate the brain's synthesis of serotonin.

Another object is to efficiently transport tryptophan across the blood-brain barrier so that an effective relief-yielding quantity of serotonin is produced within the brain.

Still another object of the invention is to provide a method and composition for promoting the conversion of tryptophan to serotonin within the brain.

Yet another object is to facilitate the activation of the enzyme tryptophan hydroxylase which, when activated, converts tryptophan into a precursor of serotonin, namely, 5-hydroxytryptophan.

Still another object is to increase the total number of available serotonin binding sites on brain membranes.

Another object is to increase the specific binding of serotonin to all available binding sites on brain membranes by increasing the bond strength between serotonin and nerve axons.

Yet another object is to provide a method and composition for relieving pain, depression, excessive appetite and insomnia by triggering the release or displacement of tryptophan from its usual protein-bound or complexed state within the blood plasma to a free, unbound state in order to increase the free tryptophan concentration in blood.

A further object is to increase both the bound and unbound (or complexed) fraction of tryptophan within blood plasma in order to maximize the amount of tryptophan transported across the blood-brain barrier into the brain for production of serotonin.

A particularly effective composition has been found to include tryptophan, a salicylate such as acetylsalicylic acid (aspirin) or magnesium salicylate, calcium, magnesium, ascorbic acid, copper, niacinamide, pyridoxine, and a carbohydrate such as a sugar. A most effective sugar has been found to be fructose, which yields a steadily metered release of insulin into the blood. A preferred single source of both calcium and ascorbic acid is available as calcium ascorbate and a preferred single source of both a salicylate and magnesium is available as magnesium salicylate.

Various other objects, features and attendant advantages of the present invention will be more fully appreciated as the same becomes better understood from the following detailed description.

DETAILED DESCRIPTION OF THE PREFERRED EMBODIMENTS

As briefly stated above, there are up to nine operative ingredients which, when combined according to the invention, yield an effective composition for promoting the transport of tryptophan from the blood plasma into the brain and for promoting the synthesis of serotonin from tryptophan within the brain. High brain levels of serotonin have been shown to increase one's pain threshold level, decrease appetite, relieve depression and promote sleep. The primary ingredient, tryptophan, may be provided in any amount ranging from about 50 milligrams per dosage up to about 12 grams per dosage. However, a preferred dosage range has been found to extend from about 50 milligrams to one gram per dosage, particularly if the dosage is repeated several times daily. A preferred dosage schedule during waking hours may range from once an hour to once every three or four hours.

In addition to the primary ingredient tryptophan, any one, several or all of the following eight types of additional ingredients may be provided to facilitate tryptophan transport into the brain and/or to promote conversion of tryptophan into serotonin. These additional ingredients may either be directly combined with tryptophan and formed as a tablet or capsule, or may be coadministered as separate ingredients. Preferably, the dosage schedule of each additional ingredient would be the same as that for the tryptophan.

The first supplemental ingredient is calcium, preferably in the form of calcium ascorbate provided in single dosage amounts ranging from 1 to 500 milligrams. Calcium may alternatively be supplementally provided as any one or any combination of the following salts of calcium within a single dosage weight range of 1 to 500 milligrams:

| | |
|---|---|
| calcium ascorbate | calcium gluconate |
| calcium carbaspirin | calcium glycerophosphate |
| calcium carbonate | calcium lactate |
| calcium caseinate | calcium pantothenate |
| calcium chloride | dicalcium phosphate |
| calcium glubionate | tricalcium phosphate |
| | calcium pyrophosphate |

A most effective dosage for the above-listed salts may vary from 10 to 100 milligrams.

When a nerve cell is stimulated, one of the first events to occur is a transient but significant increase in free intracellular calcium concentrations. Concentrations of calcium also increase in the nerve cell endings upon transmission of a nerve impulse. Calcium migrates from within the neuron fibers to the outer surfaces of the cell upon nerve stimulation thereby raising the concentration of calcium at the nerve endings. This increase in calcium signals the nerve cell to release the nerve's chemical transmitter, i.e., serotonin.

Calcium does not act alone in triggering the release of serotonin. Rather, calcium stimulates the release of neurotransmitters in concert with the protein calmodulin. Calmodulin acts as an intracellular intermediary or regulator for calcium ions. As noted above, an activated form of kinase is required for the synthesis of serotonin. The calcium ions activate kinase by combining with calmodulin on serotoninergic neurons to form a calcium-calmodulin complex. Without sufficient calcium, the transmission of the nerve impulses is impeded since insufficient kinase is activated.

Calcium not only plays a crucial role in the depolarization-induced activation of tryptophan hydroxylase as previously discussed, but also aids the binding of serotonin to nerve membranes. Whereas high concentrations of monovalent cations (greater than 20 mM of Na or K) induce a significant inhibition of serotonin binding to brain membranes, millimolar concentrations of divalent cations such as calcium ($Ca^2$) and magnesium ($Mg^2$) consistently increase the specific binding of serotonin to nerve cells responsible for transmission of nerve impulses. In addition, calcium also increases the total number of available specific binding sites for serotonin in brain membranes.

Accordingly, a calcium "window" exists between upper and lower limits of calcium concentrations wherein sufficient calcium is provided to activate kinase but not in excessive amounts which would inhibit the binding of serotonin on nerve membranes. By providing 1 to 500 milligrams of a calcium salt as specified, calcium concentrations will be maintained within this "window" range.

Another ingredient which is advantageously included in the supplemental dietary composition is a magnesium supplement, preferably in the form of magnesium salicylate in amounts ranging from 1 to 500 milligrams. Magnesium may also be provided as any one or any combination of the following salts of magnesium within a weight range of 1 to 500 milligrams:

| | |
|---|---|
| magnesium carbonate | magnesium oxide |
| magnesium gluconate | magnesium salicylate |
| magnesium hydroxide | magnesium sulfate |
| | magnesium trisilicate |

These salts are preferably administered in amounts ranging from 10 to 100 milligrams per dosage.

Nerve impulses are transmitted across the nerve synapse under the control of an on-off switching mechanism. The "on" state is energized by the production of various neurotransmitters including serotonin. Serotonin is produced in the nerve dendrites and travels across the synapse to the axon of an adjacent nerve cell. In order to effectively transmit the nerve signal from one nerve cell to another, serotonin must find a binding site on an adjacent axon. The presence of millimolar concentrations of magnesium not only increases the number of available binding sites for serotonin but also increases the strength of the resulting bonds between the neurotransmitters and the nerve cells. The result is a stronger and clearer transmission of nerve signals via enhanced transmission and binding of serotonin. This in turn results in more effective relief of the disorders associated with a tryptophan deficiency.

Ascorbic acid is another ingredient which is beneficial for promoting production of serotonin. Ascorbic acid is a hydrolase cofactor which is required for the hydroxylation of L-tryptophan to 5-hydroxytryptophan as outlined above. A preferred form or compound for supplemental ascorbic acid is calcium ascorbate which, when ingested, provides not only ascorbic acid but also the calcium required to initiate the phosphorylation of tryptophan hydroxylase. The weight range of the calcium ascorbate is preferably within 1 to 500 milligrams. Other suitable sources of ascorbic acid include:

sodium ascorbate
calcium ascorbate
niacinamide ascorbate

These alternate sources of ascorbic acid should be maintained within the 1 to 500 milligram limit specified above with a preferred range of 10 to 100 milligrams per dose.

Another ingredient which is beneficial in optimizing the production of serotonin is copper, the mineral element that serves as a co-factor in the enzymatic reaction involving tryptophan hydroxylase. A copper supplement will therefore facilitate the conversion of tryptophan into serotonin. A preferred form or compound for supplemental copper is copper gluconate which, when ingested, provides the element copper which is essential in the formation of the active enzyme complex. The weight range of the copper dosage is preferably within 0.1 to 100 milligrams. Other suitable sources of copper include:

copper sulfate
amino acid chelates of copper

The preferred dosage forms of these salts are in amounts of copper ranging from 0.1 to 100 milligrams of copper.

Niacinamide is another additional ingredient which may be included to promote or facilitate tryptophan transport into the brain. Niacin is an essential nutrient that the human body must have at all times. Because of niacin's importance, the body has evolved a method by which it can synthesize niacin from tryptophan. More particularly, 60 milligrams of tryptophan is used by the body to make each milligram of niacin. Studies in humans have shown that the amount of niacin the body gets from tryptophan amounts to about one-half of the total amount of niacin that the body needs each day, that is, about 13–19 mg. This means that from $(13/2 \times 60)$ mg to $(19/2 \times 60)$ mg or 390 mg to 570 mg of tryptophan is needed each day for its conversion to niacin.

In order to attempt to minimize the destruction of the supplemental tryptophan within the body via synthesis into niacin, a niacin supplement such as niacinamide or nicotinamide is included along with the tryptophan to provide the body with the pre-formed vitamin niacin. Furthermore, it has been learned that some of the beneficial effects of tryptophan in raising brain levels of serotonin may be diminished by a rapid breakdown (catabolism) by tryptophan pyrrolase. The administration of a tryptophan pyrrolase inhibitor such as niacinamide, nicotinamide or nicotinic acid inhibits such tryptophan breakdown in man. A practical dosage may range from 1 milligram to 100 milligrams with a preferred range of 5 to 25 milligrams.

The next operative ingredient of the invention is pyridoxine (vitamin $B_6$). Pyridoxine is essential in the tryptophan-serotonin conversion process and is part of the enzyme system which functions directly in the conversion of tryptophan to serotonin. That is, pyridoxine is a decarboxylase co-factor required for the decarboxylation of 5-hydroxytryptophan to serotonin. By providing the body with this vitamin at the same time that the supplemental tryptophan is administered, this important nutrient will be provided to individuals whose dietary intake may have been deficient. This will ensure efficient conversion of tryptophan to serotonin. Pyridoxine may be administered in dosages ranging from 0.5 to 50 milligrams, with a preferred range of 1 to 10 milligrams per dose.

The next ingredient is a carbohydrate such as a sugar, preferably the monosaccharide sugar, fructose. Investigations have shown that dietary carbohydrate causes an increase in the relative concentration of blood tryptophan levels; i.e., the amount of tryptophan is increased relative to the amount of the interfering large neutral amino acids that compete with tryptophan for the transport carrier mechanism in the brain. Of all the blood amino acids, tryptophan is the only amino acid that is carried as an albumin-bound complex. All of the other amino acids, including the LNAAs, travel in the blood as the free amino acids.

Insulin, when elaborated into the blood stream in response to an increase in blood sugar concentration serves to drive amino acids into the body tissues while the blood courses on its way to the brain. The tryptophan-albumin complex is not affected by this insulin action, and thus remains available to reach the brain. Thus, this complex is not "lost" to the body tissues. However, the other amino acids are removed from the blood thereby increasing the relative percentage of tryptophan in the blood. Carbohydrate intake, therefore, with its insulin-releasing action, helps to improve the tryptophan/LNAA ratio in favor of the tryptophan and increases the amount of tryptophan crossing the blood-brain barrier into the brain. Fructose is included in each capsule as a preferred source of carbohydrate to achieve this insulin/LNAA/tryptophan effect.

Relatively modest dosages of fructose have been found sufficient to produce the desired effects. For example, dosages of fructose as little as 5 milligrams have been found to increase the effect of tryptophan in providing relief of the disorders mentioned above. A preferred dosage ranges from 25 milligrams to one gram per dosage.

The next, but crucial, ingredient is a salicylate, preferably an oral salicylate salt. As previously noted, tryptophan is usually not transported in the blood in a free state, but rather in a bound or complexed form with the protein albumin, a plasma component. Tryptophan is the only circulating amino acid that is significantly bound to human serum albumin. It has been shown that salicylates displace tryptophan from its protein binding site on albumin in blood plasma thereby raising the free, circulating tryptophan concentration in blood. This free or unbound tryptophan is more easily converted to serotonin than the bound form and therefore its presence is most desired.

While it may seem paradoxical to release tryptophan from its complexed state with albumin through administration of a salicylate, then to drive the resulting free tryptophan into the body tissues along with the other free amino acids via administration of a carbohydrate and release of insulin, the end result of this action is an overall increase in the transport of tryptophan into the brain. The exact interaction in this case is not completely known, although the combination of the free tryptophan provided by oral administration of the composition and the free tryptophan released from serum albumin may not collectively enter the body tissues under the influence of insulin to the extent or relative percent that the other free amino acids do, thereby increasing the relative serum concentration of free tryptophan.

Moreover, since not all of the serum tryptophan is released by the salicylate from its bound state, the remaining albuminbound tryptophan is allowed to reach the brain at which point it is freed from albumin and transported into the brain by the body's own release mechanism. Thus, the combined effect of the administration of a salicylate and a carbohydrate along with free tryptophan is to increase both the absolute free fraction of circulating tryptophan and the relative amount of albumin-bound tryptophan in relation to the remaining LNAAs.

A particularly effective method of administration is to delay the tryptophan-releasing action of the salicylate until the insulin released by the carbohydrate, preferably fructose, has driven the LNAAs into the body tissues. A further advantage may be gained by delaying the administration of tryptophan until the presence of the LNAAs within the blood is decreased by the action of the insulin. This can be achieved by first administering the carbohydrate, waiting about five minutes to an hour for the insulin to reduce the concentration of LNAAs within the plasma, then administering the salicylate, tryptophan and any desired additional ingredients. The advantage gained is that the albumin-bound tryptophan will not be freed prior to the release of insulin so that the bound tryptophan will remain in the blood while the LNAAs are removed from the blood. By administering the salicylate after the carbohydrate, the tryptophan freed from the albumin will not be lost to the body tissues under the action of insulin, but will remain in the blood for transport into the brain. Moreover, by delaying the administration of supplemental tryptophan until at least five minutes after the administration of a carbohydrate, the supplemental tryptophan will not be driven into the body tissues so that the concentration of serum tryptophan may be maximized.

An alternate method of delaying the administration of the salicylate and/or the tryptophan is to microencapsulate the salicylate and/or the tryptophan by conventional processes to achieve a timed delay of these ingredients into the blood. In this manner, all ingredients may be taken orally at the same time for convenience, yet the bound and supplemental tryptophan will be protected from the initial action of the insulin.

It should be emphasized that a salicylate such as aspirin may be used according to the invention solely for its ability to safely break the bond between tryptophan and albumin in order to increase the free fraction of serum tryptophan and not for the well-known analgesic effect produced by salicylates. In fact, any salicylate administered alone in the dosages set forth below (without the additional ingredients) will not lower the threshold of pain to any degree near that when combined with any combination of or all of the ingredients identified herein.

While magnesium salicylate is the pharmaceutical agent presently preferred to effect release of tryptophan from its bound or complexed state with albumin, any other pharmaceutically acceptable oral salicylate salt such as sodium salicylate, choline salicylate or any other substance which safely produces this release would serve as well. For example, acetanilid, acetophenetidin, and aminopyrine could be used in about the same dosage as aspirin to achieve the same result. Other pharmaceutically acceptable substances have been found capable of releasing tryptophan from serum albumin and could be combined with tryptophan and the other ingredients in addition to or in place of a salicylate so as to fulfill the goal of the present invention. Such substances include heparin, isoprenaline, aminophylline, dopa, clofibrate, unesterified fatty acids, probenecid, bulbocapnine, and acetaminophen.

A particularly effective and convenient source of both magnesium and a salicylate has been found to be magnesium salicylate. This salicylate salt is generally preferred over aspirin because magnesium salicylate does not act as an anticoagulant. That is, salicylate salts do not inhibit platelet aggregation and therefore do not add an additional active agent to those patients already receiving anticoagulant medication.

The effective dosage of magnesium salicylate may range from 1 to 500 milligrams with a preferred dosage range of 10 to 200 milligrams. Choline salicylate or sodium salicylate may be substituted for magnesium salicylate in about the same dosage or dosage ranges as specified for magnesium salicylate.

While the weight percentages of each ingredient listed below could vary at least by 50% and in accordance with the amounts found to achieve an optimum effect, a preferred composition of the supplement for an effective pharmaceutically acceptable single dosage (tablet or capsule) for a typical patient is approximately as follows:

|  | Weight in mg | % by weight (approx.) |
|---|---|---|
| L-tryptophan | 200 | 43.0 |
| Fructose | 125 | 26.9 |
| Niacinamide | 10 | 2.1 |
| Pyridoxine | 5 | 1.1 |
| Calcium ascorbate | 55 | 11.8 |
| Magnesium salicylate | 55 | 11.8 |
| Copper gluconate | 15 | 3.2 |
| Total weight of tablet | 465 mg | 100% |

Because the above composition can be taken orally in amounts up to 10–12 capsules daily, the inclusion of the sugar, fructose, was deliberately selected rather than glucose or sucrose because of studies which indicate that the response of the body in releasing insulin into the blood is much more even with fructose than with the other sugars that were used and without any sudden insulin upsurge. Thus, fructose provides the desired predictability of insulin release needed for a constant production of serotonin which in turn is required for the satisfactory even relief of physiological disorders.

Treatment of physiological disorders may be carried out according to the invention with maximum sustained or prolonged daily dosages of up to:

| | |
|---|---|
| L-tryptophan | 15 grams |
| Fructose | 20 grams |
| Niacinamide (Nicotinamide, Nicotinic Acid) | 2 grams |
| Pyridoxine | 2 grams |
| Calcium ascorbate (or any other calcium salt) | 6 grams |
| Magnesium salicylate (or any other magnesium salt) | 6 grams |
| Ascorbic Acid (or any other acceptable ascorbate) | 6 grams |
| Copper gluconate (or any other copper salt) | 1 gram |
| Acetylsalicylic acid (or any other oral salicylate) | 4 grams |

These maximum dosages may be administered at one time and in any combination which includes at least L-tryptophan, a salicylate and fructose, although lesser dosages spaced over time are preferred.

Obviously numerous modifications and variations of the present invention are possible in light of the above teachings. It is therefore to be understood that within the scope of the appended claims, the invention may be practiced otherwise than as specifically described herein. For example, other carbohydrates could be used in place of fructose without departing from the spirit of the invention.

While upper daily limits have been placed on each ingredient for prolonged use of the composition, virtually no upper limit need be maintained for any ingredient for initial or intermittent treatment of physiological disorders. It has been found that initial treatment may require five to ten times the maximum normal or sustained dosages identified above in order to accelerate initial relief. Once relief is achieved, lower dosages may be maintained according to the above-specified ranges.

Moreover, it should be noted that only tryptophan, an oral salicylate, and fructose are essential to carry out the invention. The remaining ingredients are optional and may be added in any combination with the tryptophan, salicylate and fructose depending upon the dietary deficiency of a particular patient. Those patients exhibiting a deficiency in any one or a combination of the remaining ingredients may be treated only with those ingredients specifically required to overcome the patient's particular deficiency.

What is claimed is:

1. A method for treating physiological disorders responsive to treatment with L-tryptophan, wherein said method comprises:
    administering to a patient a dosage of a composition comprising L-tryptophan in an amount sufficient to increase transport of L-tryptophan into the patient's brain and a salicylate selected from the group consisting of sodium salicylate, choline salicylate and magnesium salicylate in an amount sufficient to release L-tryptophan from the patient's serum albumin, said dosage of the composition being sufficient to increase production of serotonin within the patient's brain to a level which provides relief of said physiological disorders.

2. The method of claim 1, which further comprises administering to the patient a dosage of a carbohydrate.

3. The method of claim 1, which further comprises administering to the patient a dosage of a carbohydrate, a dosage of a calcium supplement, a dosage of a magnesium supplement, a dosage of an ascorbate, a dosage of a copper supplement, a dosage of a niacin supplement and a dosage of pyridoxine.

4. A composition for increasing production of serotonin within a patient's brain, comprising a dosage of L-tryptophan in an amount sufficient to increase transport of L-tryptophan into the patient's brain, and
    a dosage of a pharmaceutically acceptable salicylate, selected from the group consisting of sodium salicylate, choline salicylate and magnesium salicylate said dosage of said salicylate being sufficient to release L-tryptophan from the patient's serum albumin, and
    said dosages combined so as to increase said production of serotonin to a level which provides relief of physiological disorders.

5. The composition of claim 4, further comprising a dosage of a carbohydrate in an amount sufficient to release insulin into the patient's blood for freeing albumin-bound L-tryptophan.

6. The composition of claim 4, further comprising a dosage of a calcium supplement for facilitating conversion of L-tryptophan into serotonin.

7. The composition of claim 4, further comprising a dosage of a magnesium supplement for enhancing the neurotransmission of serotonin.

8. The composition of claim 7, wherein said salicylate and said magnesium supplement are each provided in the form of magnesium salicylate.

9. The composition of claim 4, further comprising a dosage of ascorbic acid for facilitating hydroxylation of L-tryptophan.

10. The composition of claim 9, wherein said ascorbic acid is provided as an ascorbate selected from the group consisting of sodium ascorbate, calcium ascorbate and niacinamide ascorbate.

11. The composition of claim 4, further comprising a dosage of a copper supplement for facilitating conversion of L-tryptophan into serotonin.

12. The composition of claim 4, futher comprising a dosage of a niacin supplement for preventing synthesis of niacin from L-tryptophan.

13. The composition of claim 4, further comprising a dosage of pyridoxine for facilitating conversion of L-tryptophan into serotonin.

* * * * *